United States Patent [19]

Patrick et al.

[11] Patent Number: 5,762,797
[45] Date of Patent: Jun. 9, 1998

[54] ANTIMICROBIAL FILTER CARTRIDGE

[76] Inventors: Gilbert Patrick, 635 Dixon School Rd., Kings Mountain, N.C. 28086; Arvind S. Patil, 1030 Southwent Dr., Davidson, N.C. 28036

[21] Appl. No.: 573,067

[22] Filed: Dec. 15, 1995

[51] Int. Cl.$^6$ .................................. B01D 29/07
[52] U.S. Cl. .................. 210/497.1; 210/494.1; 210/494.2; 210/501; 210/488; 55/447
[58] Field of Search ................ 210/501, 497.1, 210/500.21, 317, 484, 488, 494.1, 494.2; 55/447

[56] References Cited

U.S. PATENT DOCUMENTS

| | | | |
|---|---|---|---|
| 3,065,856 | 11/1962 | Goldman | 210/494.1 |
| 3,327,859 | 6/1967 | Pall | 210/501 X |
| 3,828,934 | 8/1974 | Green et al. | 210/497.1 |
| 4,032,688 | 6/1977 | Pall | 210/497.1 X |
| 4,048,075 | 9/1977 | Colvin et al. | 210/494.1 |
| 4,104,170 | 8/1978 | Medza | 210/493.2 |
| 4,660,779 | 4/1987 | Nemesi et al. | 210/497.1 |
| 4,769,096 | 9/1988 | VanderGiessey et al. | 210/493.2 |
| 4,902,427 | 2/1990 | Szczepanick | 210/484 |

Primary Examiner—Ana Fortuna
Attorney, Agent, or Firm—Isaf, Vaughan & Kerr

[57] ABSTRACT

An antimicrobial filter cartridge having a perforated core member wrapped with a microporous membrane, which is overwrapped with a spiral wrapping of an antimicrobial agent impregnated yarn. The spiral wrapping is covered with a criss-cross wrapping of yarn. The filter cartridge is sized so as to fit tightly into a cartridge housing of a fluid filtration system. Fluid passing through the cartridge housing will be filtered by the filter cartridge to remove microorganisms from the water and which prevents the growth of microorganisms on the filter media.

20 Claims, 4 Drawing Sheets

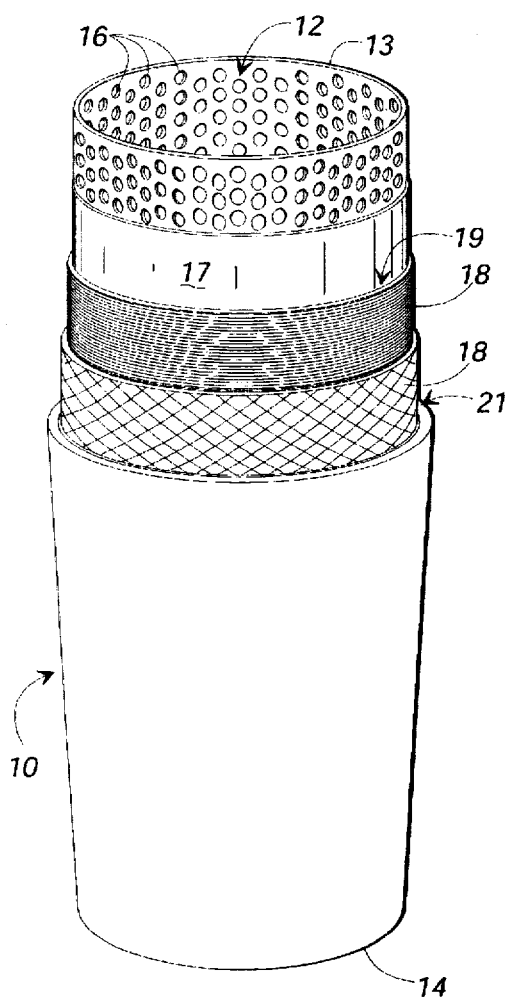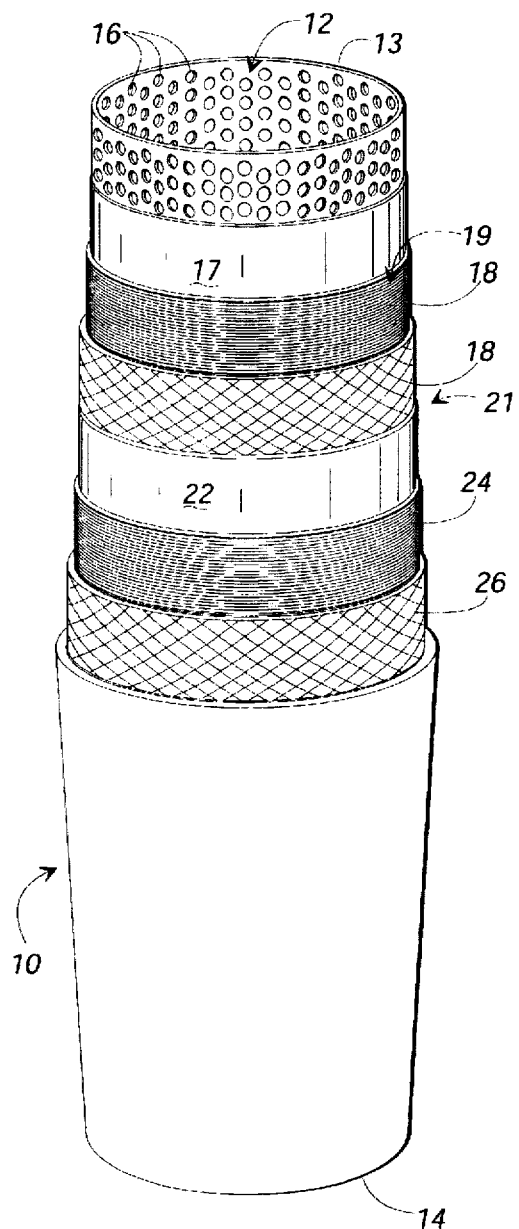
FIG. 1      FIG. 2

ANTIMICROBIAL FILTER CARTRIDGE

FIELD OF THE INVENTION

This invention relates generally to filters for the purification of liquids. In particular, the present invention relates to an antimicrobial filter cartridge for a filtration system for removing microorganisms from water and which is formed from layers of yarns and nonwoven webs or mats wound or wrapped in varying patterns and treated with an antimicrobial agent to enable the filter cartridge to trap and remove low micron organic contaminant particles and prevent the growth of the trapped microorganisms on the filter cartridge media to significantly reduce the level of contaminants and bacteria within the water flowing through the filtration system.

BACKGROUND OF THE INVENTION

In recent years, the public has been increasingly aware of the deteriorating quality of our nation's water supply. Municipalities are requesting the EPA to lower the standards of tap water to a much lower quality. Medical patients with low immunity are requested not to drink tap water. The major part of the contamination of the drinking water is bacterial in nature.

All over the world, countries with increasing populations are concerned that the water quality has deteriorated to an all time low. However, many known solutions that exist to purify water are too expensive or are not feasible in certain locations.

Reverse osmosis systems are one of the most common solutions for the improved water quality. Generally, these systems use a sediment removal filter in conjunction with activated carbon and a bacteriostatic membrane coated with oxides and halide of silver, as described in detail by Nishino in U.S. Pat. No. 3,872,013, placed between the filter and the water outlet. The membrane will prevent certain bacteria from leaving the filter and will retard their growth on the surface of the membrane, but will not check their growth on the activated carbon and their ability to multiply and produce toxins. This also holds true for other mechanical filters such as ceramic filter cartridges that filter out bacteria of about 1 micron in size, but are ineffective in retarding bacteria growth as the bacteria are collected on the surface of the filter.

Another type of biocidal reverse osmosis system is described in detail by Medlin in U.S. Pat. No. 5,269,919. Medlin describes how a polyiodide resin releases iodide upon contact with bacteria and viral organisms and use granular metal alloys and activated carbon to remove iodides released in the water. If not removed, these iodides would be harmful internally to human beings. EPA "Policy on Iodine Disinfection", initially developed in 1973 and reaffirmed in 1982, is that iodine disinfection is for short-term only, whenever iodine-containing species remain in the drinking water.

In view of the foregoing, it would appear that present water purification systems become a breeding ground for bacteria and toxins or would subject users to the possibility of trace metals such as silver and copper, and other contaminants not filtered out of the water.

It therefore can be seen that a need exists for a water filter cartridge to filter microscopic organisms and prevent their growth within the filter media, without releasing life harming biocides that have to be further filtered out.

SUMMARY OF THE INVENTION

Briefly described, the present invention comprises a filter cartridge for a water filtration system for safely and effectively filtering microorganisms from drinking water and prevents the further growth of the microorganisms trapped by the filter. The filter cartridge includes an inner tubular-shaped perforated core of a metal, plastic or ceramic material, or formed from activated carbon. The core is covered with a microporous membrane having nominal pores of approximately $0.45\mu$ to $0.10\mu$. The membrane is tightly wrapped around the core so that there are no spaces created between the membrane and the core, and preferably is slightly wider than the length of the core so as to overlap the two opposing ends of the core.

A yarn or nonwoven material that has been impregnated or otherwise treated with an antimicrobial agent typically is tightly, spirally wound about the membrane so that there are no spaces between the turns or layers of the yarn and thus there are no voids between the yarn and the microporous membrane, forming a primary spiral yarn layer. Thereafter, another layer of antimicrobial yarn is then wrapped around the spiral layer in the standard criss-cross or diamond-wrap pattern, creating diamond-shaped openings through which water can travel. It is also possible to wrap the microporous membrane with a nonwoven fibrous material mat or web containing the antimicrobial fiber, thus replacing the yarn. Alternatively, any filling material that affords a large surface area, covered with or impregnated with antimicrobial agent, can be used in place of the yarn.

In addition, the criss-cross layer can be covered with a second microporous membrane, also having a nominal pore size of $0.45\mu$ or less, followed by a second spiral layer of antimicrobial yarn and a second or outer criss-cross wound section of antimicrobial yarn. The outer criss-cross wound section is formed with sufficient thickness so that the filter cartridge can be tightly inserted into a cartridge housing, with minimal space between the filter cartridge and the housing walls. The ends of the membrane and yarn layers of the finished filter thereafter are sealed with an antimicrobial polymer or resin, forming end caps at the opposite ends of the filter, to ensure the fluids will pass through the entire filter before exiting the system.

The filter cartridge is installed within a housing for a filtration system connected to a water supply. As water flows into the housing, the water flows down and through the filter cartridge, and exits the housing through an outlet port. The filter cartridge of the present invention removes microorganisms and other impurities from water flowing through the cartridge. Large impurities generally are removed by the criss-cross layers or by the microporous membranes. Microorganisms retained by one of the membranes are forced into contact with the antimicrobial agent in the yarn because the tight spiral wrapping creates minimal void spaces between the yarn and the membrane. Thus, sufficient contact between the contaminants and the antimicrobial treated yarn to remove and treat the contaminants is achieved without requiring long contact times between the fluid flow and filter cartridge. An equally effective antimicrobial filter further can be obtained using a microporous ceramic candle or an extruded activated carbon core, without a microporous membrane as described above, as long as the effective nominal size of the pores of the ceramic candle or carbon core is less than $0.45\mu$.

It is, therefore, an object of the present invention to provide an antimicrobial filter cartridge that overcomes the above-discussed and other deficiencies of the prior art by providing a filter cartridge that substantially completely filters microorganisms from water and prevents the growth of the microorganisms within the filter media.

It is another object of the present invention to provide an antimicrobial filter cartridge that does not release harmful toxins into the water that must be removed from the water before the water can be safely consumed.

A further object of the present invention is to provide an antimicrobial filter cartridge that can be used in presently available filtration system housings including those used in reverse osmosis systems that will inhibit the growth of microorganisms and subsequent toxin production and will protect the activated carbon filter commonly used in reverse osmosis filtering systems.

A still further object of the present invention is to provide an antimicrobial filter cartridge having very little dead space but with sufficient water flow.

Another object of the present invention is to provide an antimicrobial filter cartridge wherein nearly all of the water flowing into the filter cartridge comes into contact with an antimicrobial agent.

Other objects, features, and advantages of the present invention will become apparent to one with skill in the art upon examination of the drawings and the detailed description.

BRIEF DESCRIPTION OF THE DRAWINGS

FIG. 1 is a side elevational view of a preferred embodiment of the present invention, with portions cut away.

FIG. 2 is a side elevational view of a second embodiment of the present invention, with portions cut away.

DETAILED DESCRIPTION

Figure 3:
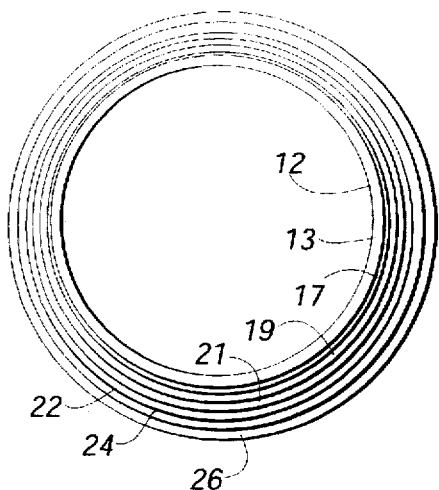
FIG. 3 is a cross-sectional view of one end of the embodiment of the filter cartridge of FIG. 2.

Referring now to the drawings in which like numerals indicate like parts throughout the several views, FIG. 1 illustrates a preferred embodiment of a filter cartridge 10 constructed in accordance with the present invention. The filter cartridge 10 includes a hollow central perforated core 12 having open ends 13 and 14, and which can be formed from plastic, paper, or metal. Alternatively, the core can be manufactured of compressed activated carbon or ceramic candles, which are inherently perforated. The core is formed as a tube or cylinder approximately 5 to 30 inches in length and generally having a diameter of approximately 1 to 2 inches, although larger or smaller diameters can be used if necessary. A series of pores or perforations 16 are formed through the core along its length.

A first microporous membrane 17 is wrapped tightly around the core so as to cover it completely. Preferably, the membrane 17 is a thin film having a width slightly greater than the length of the core 12 so that the membrane overlaps each of the open ends 13 and 14 of the core by approximately 0.125 inches. The microporous membrane has a series of pores of a nominal size of about between approximately 5.0μ to 0.10μ, preferably 0.45μ to 0.10μ or less, so that it will effectively keep most gram positive and gram negative bacteria and containment particles larger than 0.45μ to 0.10μ from flowing through the membrane into the interior of the perforated core. The membrane can be one such as a polysulfone membrane sold by Memtec America Corp. under the trade name Filtrite®. For cores formed from carbon or ceramic material, the microporous membrane potentially can be eliminated if the effective size of the pores or perforations inherently formed in the carbon and/or ceramic cores are less than 0.45μ.

A fibrous yarn 18 is wrapped in a close, tight spiral winding over the microporous membrane 17 along the length of the underlying perforated core to form a first spiral wound layer 18. The yarn typically is formed from spun 3 dpf, 2" fibers of white polypropylene, polypropylene, cellulose acetate, rayon, lyocell, acrylic, polyester or any other fibrous material that will support the antimicrobial agent. For some applications, the yarn further can be formed from nylon, cotton or a fibrillated filament yarn material. In addition, a yarn made from combinations of these polymers can be used to form the primary spiral wound yarn layer. The yarn is impregnated with an antimicrobial agent for example, during its spinning and formation. Preferably, the antimicrobial agent which is used is mixed with the yarn during formation of the fibers so that it is dispersed throughout the yarn fibers and will diffuse to the surface of the fibers during use of the filter cartridge.

The yarn used in the filter cartridge of the present invention can be between 10/1 c.c. to 0.3/1 c.c., preferably between 3/1 c.c. to 0.4/1 c.c. The yarn further can be made from fibers such as polypropylene, acrylic, cellulose acetate, nylon, polyester, rayon, lyocell, cotton or combinations and blends thereof. The deniers of these fibers can be between 0.3 dpf to 10 dpf, the preferable range based on cost and performance being 1.5 dpf to 6 dpf. These fibers typically are rendered antimicrobial, either by treating them topically or by impregnating them with the antimicrobial agent during their extrusion. The concentration of the antimicrobial agent in the fibers generally is between 100 to 10,000 ppm, preferably between 2000 ppm to 8000 ppm. The antimicrobial content of the final filter cartridge based on the yarn content should be between 100 ppm to 10,000 ppm, preferably between 2500 ppm to 7500 ppm.

Preferably, the antimicrobial agent is practically insoluble in the water passing through and over the filter cartridge, and is safe, non-toxic, non-carcinogenic, non-sensitizing to human and animal skin and does not accumulate in the human body when ingested. Generally, the antimicrobial is a broad spectrum antimicrobial agent, i.e., it is equally effective against the majority of harmful bacteria encountered in water. For example, an antimicrobial agent such as 2,4,4'-trichloro-2'-hydroxy diphenol ether, or 5-chloro-2phenol (2,4 dichlorophenoxy) commonly sold under the trademark MICROBAN®B, by Microban Products Co. generally is used. However, it will be understood various other antimicrobial agents can be used in the present invention.

The yarn 18 is wrapped in a single tight spiral wrapping or winding layer 19, wrapped so that there is no space between each of the individual turns or layers and so that there are no spaces between the first spiral wrapping or winding 19 and the microporous membrane 17.

After the first spiral wrapping layer 19 has been applied, the same strand of antimicrobial impregnated yarn 18 can be used to wrap the filter cartridge in standard criss-cross or diamond-shaped wrapping wound in a standard pattern to form a first criss-cross wrapping layer 21. The criss-cross wrapping layer 21 does not have to be impregnated with the same antimicrobial agent impregnated yarn and can be made from non-antimicrobial impregnated yarn. Additionally, the criss-cross wrapping layer can be applied directly over the membrane without the spiral wrapping layer of yarn being applied.

The thickness of the criss-cross wrapping layer will determine the thickness of the filter cartridge. Preferably, the criss-cross wrapping layer is approximately ¼" thick, although the total thickness of the criss-cross wrapping layer 21 can be of greater or lesser thicknesses, depending on the size of the filtration system housing in which the filter cartridge is to be installed, so as to enable the filter cartridge to fit tightly into a housing of a filtration system. Once the filter has been wrapped to the desired, finished thickness, the yarn is cut and the end is tucked under or otherwise secured to a previous strand to prevent the yarn from unraveling.

In an additional embodiment, shown in FIGS. 2 and 3, the first criss-cross wrapping layer 21 can be wrapped with a second microporous membrane 22, a second spiral wrapping layer 24, and a second section of criss-cross wrapping 26 wound in a standard pattern. In this way, greater filtration ability is provided and if one of the microporous membranes is punctured or otherwise made permeable to particles under 0.45µ in size, the other membrane will act to trap and remove such particles.

Figure 4:
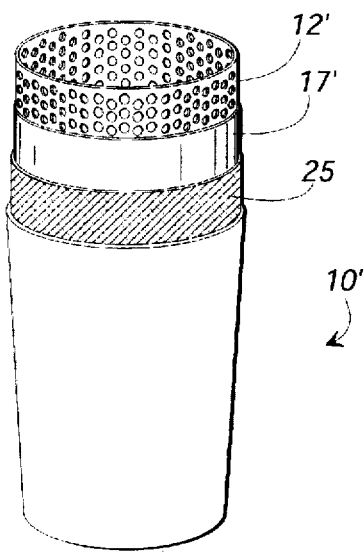
FIG. 4 is a side elevational view of an additional embodiment of the present invention, with portions cut away.

An additional embodiment of the present invention is illustrated in FIG. 4. In this embodiment, the filter cartridge 10' includes a perforated core 12' formed from plastic, paper, metal, ceramic or an activated carbon material about which is applied a microporous membrane 17'. A nonwoven fibrous mat or web 25 of a plastic or fibrous material such as nylon, polypropylene, acrylic, cellulose acetate, polyester, lyocell, rayon, cotton, etc., is wrapped about the microporous membrane and core. The nonwoven mat is treated with an antimicrobial agent such as MICROBAN®B or similar antimicrobial and is applied in a thickness sufficient to provide the filter cartridge with sufficient thickness to fit snugly within the filter housing of a fluid filtration system. For filter cartridges using a ceramic, plastic or activated carbon material, the nonwoven material further can be extruded over a ceramic, plastic or carbon mandrel.

Figure 5:
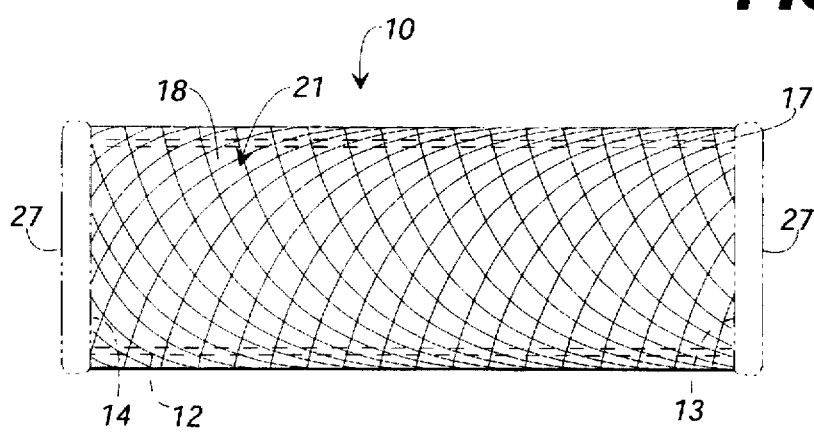
FIG. 5 is a side elevational view of the filter cartridge of the present invention.
Figure 6:
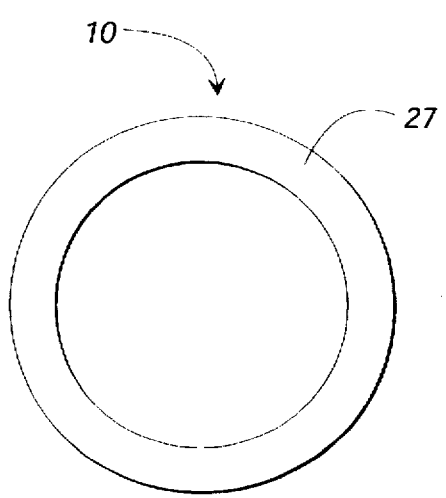
FIG. 6 is an end view of the filter cartridge of the present invention with an end cap installed.

As shown in FIG. 5, the antimicrobial membranes 17 and 22 overlap the ends 13 and 14 of the core. End caps 27 are applied over the open ends 13 and 14 of the core and the cartridge filter to seal the ends of the filter cartridge. The end caps 27 generally comprise a polyvinyl chloride (PVC) plastisol material containing an antimicrobial agent such as MICROBAN®B. The plastisol is poured in a liquid form into a shallow mold having an opened inside tube. A first end of the filter cartridge 10 is then set into the mold containing the plastisol liquid heated to a recommended temperature, for example 260° F., for approximately seven minutes or until the plastisol has sufficiently permeated the yarn at the ends of the filter. The filter cartridge is removed and its opposite or second end is dipped into the plastisol liquid. The plastisol liquid is allowed to cool and solidify over the ends of the filter cartridge, whereupon the plastisol adheres to the fibrous yarn and to the protruding edges of the microporous membrane to seal the edges of the yarn and membrane at the ends of the filter cartridge, while still leaving the center of the cartridge open as shown in FIG. 6.

In an alternative embodiment, preformed end caps may be used in place of the end caps formed from the plastisol liquid to form the end caps. Such preformed caps generally are formed from a plastic material, such as polypropylene or similar material, treated with an antimicrobial agent. The caps are formed to ensure sealing of the ends of the microporous membrane and applied to the ends of the filter cartridge, preferably with an antimicrobial adhesive.

The end caps seal and cover the ends of the microporous membrane, spiral wrapping yarn layer and criss-cross wrapping layer of the filter cartridge of each end thereof. This forces the water or other fluid being filtered through the filtration system to pass through the sides of the filter cartridge to ensure that the water or other fluid will pass through and contact the antimicrobial yarn of the criss-cross and spiral wrapping layers of yarn about the filter and through the microporous membrane so that contaminants of at least 0.1 micron or larger are trapped and removed from the flow of water passing through the filter cartridge, and the bacteria and other microorganisms therein will be eliminated by contact with the antimicrobial surfaces of the yarn layers to substantially clean the water flow of bacteria and other contaminants.

Additionally, if the water flow through the filter cartridge is to be reversed, flowing from inside of the cartridge out the sides thereof, the layering of the antimicrobial yarn/nonwoven material and the microporous membrane over the core is reversed. Thus, the core first is wrapped with the antimicrobial yarn/nonwoven mat, then overlaid with the microporous membrane. As a result, the water first will contact the antimicrobial yarn, to kill bacteria therein and thereafter contacts the microporous membrane, which traps and removes contaminant particles from the water flow. With such a construction, the filter cartridge of the present invention still provides a substantial cleaning of the water flow passing therethrough without a significant reduction in the amount of contaminants and bacteria removed from the water flow.

Figure 7:
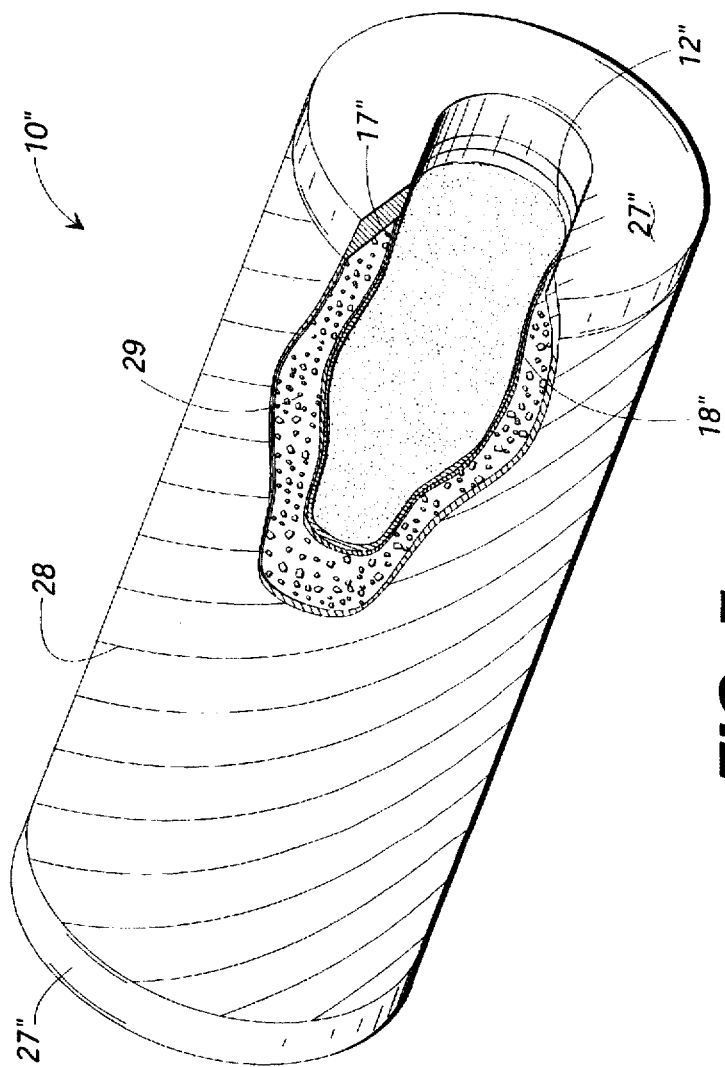
FIG. 7 is a perspective view of an additional embodiment of the filter cartridge of the present invention.

FIG. 7 illustrates still a further embodiment of the filter cartridge 10" of the present invention. In this embodiment, the filter cartridge 10" includes a perforated inner tubular core 12" formed from plastic, paper, metal, compressed activated carbon or ceramic candles. Typically, a microporous membrane 17" is wrapped about the perforated inner core 12", with the microporous membrane generally being a thin film having a series of pores of approximately 0.45µ to 0.10µ or less, such as a polysulfone membrane, and can further be treated with an antimicrobial agent if desired. An outer layer of an antimicrobial layer yarn 18" is wrapped about the core and membrane. The yarn typically is wrapped in either a spiral or criss-cross type pattern or other desired pattern covering the microporous membrane. An outer shell 28 is received over the yarn layer 18", with the shell spaced from the yarn layer to form a void or space therebetween. The shell typically is formed from a plastic such as PVC and is substantially porous, having pores of approximately 1µ–5µ formed therein. An activated carbon filling 29, generally formed from particles of activated charcoal, and treated with an antimicrobial agent, is received within the void between the antimicrobial yarn and the outer shell. Thereafter, end caps 27" are applied over the ends of the filter cartridge 10" to seal the void and the ends of the filter cartridge. With such construction, as the bacteria and particular contaminants are passed through the sides of the filter, the bacteria are contacted by and neutralized by the antimicrobial yarn and the charcoal carbon filling, as the contaminant particles also are filtered out of the water flow by the activated carbon filling in the microporous membrane. In addition, the filter cartridge also can be formed without the antimicrobial yarn, and with the antimicrobial treated, activated carbon filling applied between the membrane and the outer shell.

OPERATION

Figure 8:
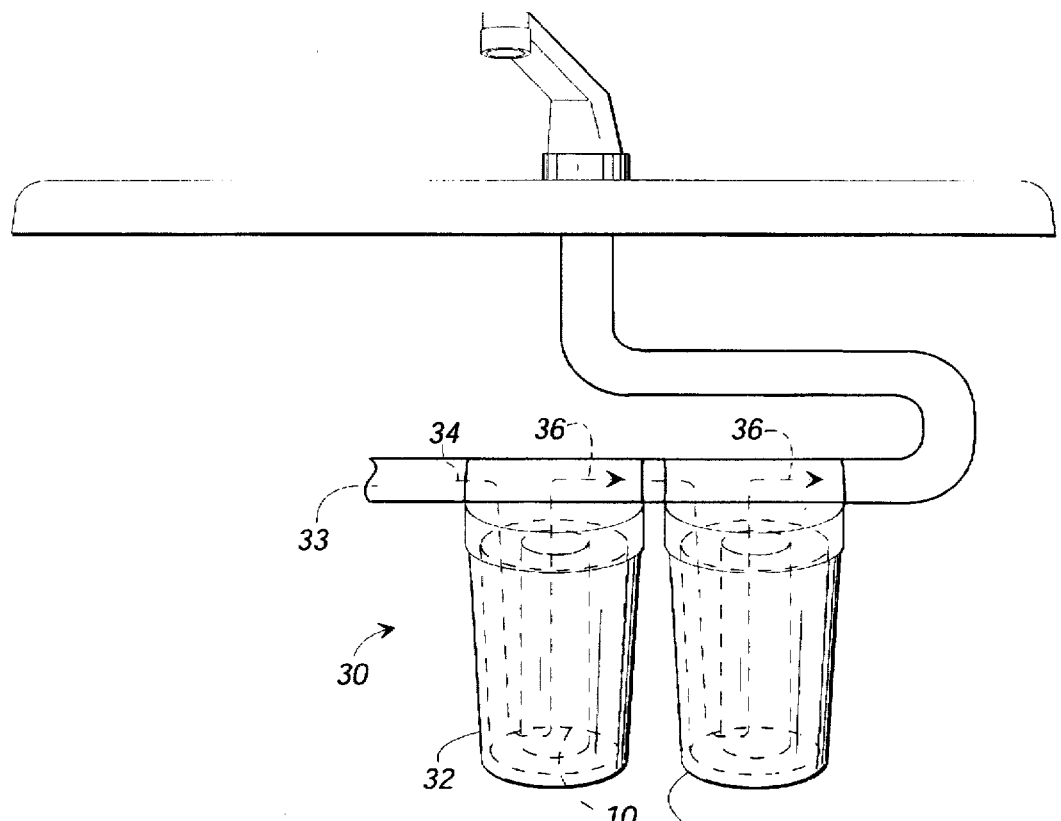
FIG. 8 is a schematic illustration of the filter cartridge of the present invention, showing the filter cartridge installed and used in an undersink filtration system.
Figure 9:
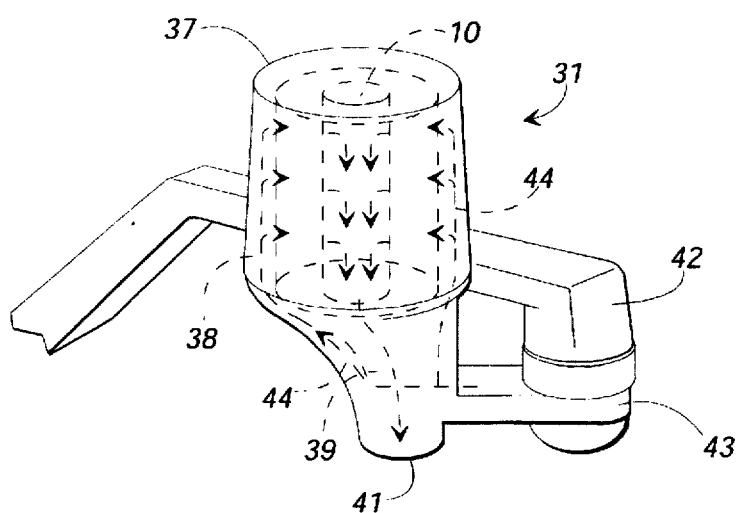
FIG. 9 is a schematic illustration of the filter cartridge of the present invention, showing the filter cartridge installed and used in a faucet filtration system.

In use, the filter cartridge 10 typically is mounted within the housing of a conventional water filtration system such as undersink system 30 as shown in FIG. 8 or in a faucet mounted filtration system 31 as shown in FIG. 9. In the system of FIG. 8, the filter cartridge 10 is fitted snugly inside the filter cartridge housing 32 and the filtration system 30 is connected to a water source 35 at the inlet end 34 of the housing. The water is supplied to the filtration system at a desired flow rate and flows into the upstream or inlet end of the housing as indicated by arrows 36. The water flows through the filter cartridge and out of the housing, whereupon the filter cartridge traps and removes particulate contaminants and bacteria within the water flow to clean and purify the water flow before the water flow exits the housing 32 through an outlet port 37. An additional filter cartridge 32 housing can be mounted downstream from the housing 32 for further cleaning.

In the water filtration system 31 of FIG. 9, the faucet mounted filtration system includes a housing 37 through which is formed internal flow passages 38 and 39. An outlet port or spout 41 is formed at the base of the housing and communicates with the outlet flow passage 39. The housing is connected to a faucet 42 by connecting portion 43 which fits over the outlet end of the faucet and which channels a flow of water therethrough and into the housing. As FIG. 9 illustrates, as the water flows into the filtration system from the faucet 42, it is directed along inlet flow passages 38, as indicated by arrows 44, through the filter 10 and out through the outlet flow passage 39 through the outlet port 41 with the water having been substantially cleaned and purified by the filter cartridge.

In the use of the filter cartridge 10 of the present invention in both of the filtration systems discussed above, the flow of water, indicated by arrows 36 (FIG. 8) and 38 (FIG. 9), is illustrated as passing through the sides of the filter cartridge and out the open ends of the core. It will, however, be understood by those skilled in the art that the filter cartridge of the present invention functions equally well if the water flow were to be reversed so as to flow in through the ends of the cartridge and out through the sides of the cartridge, without affecting the ability of the cartridge to trap and retard bacteria within the flow. Under the alternate flow conditions the sequence of membrane and antimicrobial yarn may have to be altered.

Examples of the effectiveness of the present invention for cleaning and purifying a fluid flow are discussed below.

EXAMPLE #1

A 1⅛ inch diameter, 10 inch long perforated polypropylene tube was secured in a rotatable mandrel. A microporous nominal 0.3μ membrane was wrapped around the core so that it completely covered the core and protruded from either end for about 0.125 inches. A yarn spun from a 3 dpf, 2 inch staple polypropylene fiber treated with MICROBAN®B antimicrobial agent was opened, carded, and friction spun into a 0.60 cc yarn of a bulky nature. This yarn was then tightly spiral wrapped or wound onto the microporous membrane along the entire length of the core by hand turning the mandrel. The diameter of the filter cartridge was then increased by about ¼ inch with a normal criss-cross winding. A second microporous membrane then was wrapped around the partially completed filter and a second spiral wrap layer of the same antimicrobial yarn was wound over the membrane, and then a second section of a nominal 1 micron criss-cross winding was applied, until a diameter was achieved to snugly fit the cartridge filter into a housing. The filter was sealed at either end with a MICROBAN®B treated black PVC plastisol.

A filter made as above was also made using yarns comprising 50% untreated polypropylene and 50% 3 dpf 2 inch polypropylene fiber treated with MICROBAN®B. Filters were also made using yarns comprising 50% untreated polypropylene and 50% 3 dpf 2 inch staple acrylic fiber treated with MICROBAN®B and yarns comprising 50% untreated polypropylene and 50% 3 dpf 2 inch antimicrobial cellulose acetate fiber treated with MICROBAN®B, and tested using AATCC Method 147-1993.

RESULTS

| SAMPLE IDENTIFICATION | S. aureus | K. pneumoniae |
|---|---|---|
| 1. 50% polypropylene, 50% AM acrylic | I/25 mm | I/24 mm |
| 2. 50% polypropylene, 50% AM cellu. acetate | I/24 mm | I/19 mm |
| 3. 50% polypropylene, 50% AM polypropylene | I/23 mm | I/19 mm |
| 4. 100% AM polypropylene | I/26 | I/26 mm | where I = Inhibition of growth under the sample and mm = Zone of inhibition reported in millimeters.

These results show that it is not always necessary to use yarns with 100% antimicrobially treated fiber and one can obtain comparable results using blends where cheaper untreated fiber can be substituted. Furthermore it is possible to obtain comparable results using yarns made with blends of dissimilar fibers.

EXAMPLE #2

The filter cartridge of EXAMPLE #1 (containing two microporous membranes and yarn made with 100% MICROBAN®B treated polypropylene fiber) was mounted in the housing of the cartridge assembly (made by Keystone Filter—Model 21N) that was connected by a plastic hose to a source of tap water. The water flow downstream of the filter cartridge was adjusted at 2 gal per minute. Another plastic hose was connected to the downstream spout of the cartridge housing in order to collect water samples periodically. A liquid culture of Coliform bacteria was obtained with the known concentration of the bacteria and periodically a known quantity, ca 0.5 million colony forming units (CFU), was injected on the upstream side of the cartridge housing. After letting the water flow through the filter for about 5 minutes, a sample of water was collected on the downstream of the filter and was examined using the Standard Total Coliform Membrane Filter Procedure (Am. Public Health Assoc.) for the presence of bacterial colonies. This sequence of steps was repeated for 6 times in total, till about 3 million CFU of Coliform bacteria were put through the filter of this invention.

RESULTS

The antimicrobial efficiency of the filter cartridges made as above was determined using Standard Total Coliform Membrane Filter Procedure, using an upstream water source containing injected quantities of coliform bacteria. Typically about 0.5 million cfu coliform bacteria was injected on the upstream side of the cartridge housing. After letting the water flow through the filter for about five minutes, a sample of water was collected on the downstream of the filter, and examined by the total coliform membrane filter method for the presence of bacterial colonies. No coliform bacteria was detected in the downstream water even after six injections of about 0.5 million cfu bacteria each. The results from all of the filter cartridges were the same. In addition, samples of water taken upstream of the filter but within the housing were analyzed after the above injections of coliform bacteria and after the filter had sat for 48, 72, and 96 hours. After 48 hours, 98 coliform colonies (cfu per cc) were present. After 72 hours, this number was down to 14, and after 96 hours, there were zero cfu per cc.

Less than 50 parts per billion (ppb) MICROBAN®B was detected in water downstream of the filter cartridge. About 120 ppb MICROBAN®B was detected from water which was allowed to stand for 72 hours in the cartridge housing. This amount of MICROBAN®B is not harmful to humans.

It will be obvious to those skilled in the art that many variations may be made in the above embodiments here chosen for the purposes of illustrating the present invention, and full result may be had to the doctrine of equivalents without departing from the scope of the present invention, as set forth in the following claims.

We claim:

1. An antimicrobial filter cartridge, comprising:
   an inner perforated core member;
   a microporous membrane surrounding said core member;
   an antimicrobial yarn wound about said membrane, in a spiral winding such that each winding turn of said yarn contacts its adjacent turns so as to minimize spacing between said antimicrobial yarn and said membrane; and
   at least one layer of yarn wrapped around said spiral layer in a criss-cross pattern wrapping.

2. The filter cartridge of claim 1, further comprising a second microporous membrane surrounding said criss-cross wrapping, a second spiral wrapping surrounding said second microporous membrane and a second criss-cross wrapping around said second spiral wrapping.

3. The filter cartridge of claim 1, wherein said core member is selected from the group consisting of activated carbon, plastic, paper, metal and ceramic.

4. The antimicrobial filter cartridge of claim 1, wherein said microporous membrane has nominal pores of a size between approximately 0.1μ to 5.0μ.

5. The filter cartridge of claim 1 and further including end caps applied to the filter cartridge at opposite ends thereof.

6. The antimicrobial filter cartridge of claim 1, wherein said antimicrobial yarn is made from a polymer selected from the group consisting of nylon, polypropylene, cellulose acetate, rayon, lyocell, acrylic, polyester, polyethylene, and mixtures thereof.

7. The antimicrobial filter cartridge of claim 1, wherein said antimicrobial yarn comprises cotton.

8. The antimicrobial filter cartridge of claim 1, wherein said criss-cross wrapping yarn is treated with an antimicrobial agent.

9. The antimicrobial filter cartridge of claim 1, wherein said antimicrobial yarn comprises a yarn impregnated with an antimicrobial agent selected from the group consisting of 2,4,4-trichloro-2-hydroxy diphenol ether and 5-chloro-2phenol (2,4 dichlorophenoxy) compounds.

10. An antimicrobial filter cartridge, comprising:
    an inner tubular perforated core member having a first end and a second end;
    a microporous membrane surrounding said core member overlapping said first and second ends of said core member and having nominal pores of between approximately 0.1 to 5.0 microns;
    a first layer of an antimicrobial yarn tightly wound about said membrane in a desired pattern and treated with an antimicrobial agent;
    a second layer of yarn wound about said first layer of antimicrobial yarn in a desired pattern; and
    whereby as a fluid passes through the filter cartridge, the fluid contacts the antimicrobial yarn and microporous membrane to an increased extent to enhance trapping of contaminant particles within the fluid by the yarn and membrane and to retard bacterial growth to clean the fluid of contaminants.

11. The filter cartridge of claim 10 and the antimicrobial filter cartridge of claim 1, wherein said first and second layers of antimicrobial yarn are made from a polymer selected from the group consisting of nylon, polypropylene, cellulose acetate, rayon, lyocell, acrylic, polyester, polyethylene, and mixtures thereof.

12. The filter cartridge of claim 10 and the filter cartridge of claim 1, further comprising a second microporous membrane surrounding said second layer of yarn, and an antimicrobial yarn wrapping surrounding said second microporous membrane.

13. The filter cartridge of claim 10 and wherein said microporous membrane overlaps said first and second ends of said core approximately 0.125 inches.

14. A bactericidal filter cartridge, comprising:
    a core formed from an activated carbon material and having an outer side surface and an inner side surface;
    a microporous membrane applied to said outer side surface of said core;
    a layer of antimicrobial yarn tightly spirally wound about said membrane applied to said outer side surface of said core to substantially minimize spacing between said antimicrobial yarn and said membrane;
    a layer of yarn wound about said core in a substantially criss-cross winding pattern; and
    end caps applied at opposite ends of said core.

15. The bactericidal filter cartridge of claim 14 and wherein said microporous membranes project over said opposite ends of said core approximately 0.125 inches.

16. The bactericidal filter cartridge of claim 14 and said yarns of said spiral wound and said criss-cross wound layers are formed from a polymer selected from the group consisting of nylon, polypropylene, cellulose acetate, rayon, lyocell, acrylic, polyester, polyethylene and combinations thereof.

17. The bactericidal filter cartridge of claim 14 and wherein said microporous membrane includes nominal pores of approximately 0.1 to 5 microns.

18. The bactericidal filter cartridge of claim 14 and wherein the antimicrobial yarn comprises a fibrillated filament yarn.

19. The bactericidal filter cartridge of claim 14 and wherein the antimicrobial yarn comprises a fibrillated filament yarn is impregnated with an antimicrobial agent in a concentration of approximately 100 to 10,000 ppm.

20. An antimicrobial filter cartridge, comprising:
    an inner perforated core;
    a microporous membrane applied about said core and having a series of nominal pores of approximately 0.45μ to 0.10μ;
    and antimicrobial yarn wound about said membrane in a desired pattern;
    an outer shell received over said yarn, spaced therefrom and generally formed from a substantially porous material;
    an activated carbon filling received between said antimicrobial yarn and said outer shell and generally treated with an antimicrobial agent; and
    means for enclosing opposite ends of the filter cartridge to seal said filling material therein.

* * * * *